United States Patent [19]

Hamprecht et al.

[11] 4,425,152
[45] Jan. 10, 1984

[54] 2H-1,2,4,6-THIATRIAZIN-3-ONE-1,1-DIOXIDES AND THEIR USE FOR CONTROLLING UNDESIRABLE PLANT GROWTH

[75] Inventors: Gerhard Hamprecht, Weinheim; Rolf-Dieter Acker, Leimen; Bruno Wuerzer, Otterstadt, all of Fed. Rep. of Germany

[73] Assignee: BASF Aktiengesellschaft, Fed. Rep. of Germany

[21] Appl. No.: 410,840

[22] Filed: Aug. 23, 1982

[30] Foreign Application Priority Data

Aug. 28, 1981 [DE] Fed. Rep. of Germany ....... 3134141

[51] Int. Cl.³ .................... C07D 285/00; A01N 43/72
[52] U.S. Cl. ............................................. 71/91; 544/7
[58] Field of Search ............................... 71/91; 544/7

[56] References Cited

U.S. PATENT DOCUMENTS 4,013,447 3/1977 Kay ......................................... 544/7
4,316,014 2/1982 Hamprecht et al. ..................... 544/7

Primary Examiner—John M. Ford
Attorney, Agent, or Firm—Keil & Witherspoon

[57] ABSTRACT 2H-1,2,4,6-Thiatriazin-3-one,1,1-dioxides of the formula

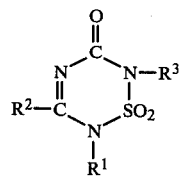

where $R^1$, $R^2$ and $R^3$ have the meanings given in the description, are used for controlling undesirable plant growth.

9 Claims, No Drawings

2H-1,2,4,6-THIATRIAZIN-3-ONE-1,1-DIOXIDES AND THEIR USE FOR CONTROLLING UNDESIRABLE PLANT GROWTH

The present invention relates to 2H-1,2,4,6-thiatriazin-3-one-1,1-dioxides, herbicides which contain these compounds as active ingredients, and a process for controlling undesirable plant growth by means of these compounds.

Substituted 5,6-dihydro-1,2,4,6-thiatriazin-5-one-1,1-dioxides have been disclosed as active ingredients for crop protection agents (German Laid-Open Application DOS No. 1,946,262). Herbicidal 5,6-dihydro-1,2,4,6-thiatriazin-5-one-1,1-dioxides are disclosed in German Laid-Open Applications DOS No. 2,508,832 and DOS No. 2,933,889. In addition, J. Chem. Res. (1977), 2,813–2,825 describes the preparation of 2-methyl- and 2-isopropyl-5-methyl-2H-1,2,4,6-thiatriazin-3-one-1,1-dioxide, without giving any information concerning the possible use of these compounds. The latter publication points out that cyclization is very difficult to carry out and requires substantial experimental effort, the yield being only 22 and 26%, respectively. 2-Isopropyl-5-phenyl-2H-1,2,4,6-thiatriazin-3-one-1,1-dioxide is obtained in a yield of only 18% when N-carboethoxybenzamidine is reacted with isopropylaminosulfonyl chloride in tetrahydrofuran at −70° C. and the product is cyclized with sodium ethylate (J. Chem. Res. (1977), 2,826–2,836).

We have found that 2H-1,2,4,6-thiatriazine-3-one-1,1-dioxide derivatives of the formula

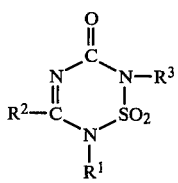
(Ia)

where $R^1$ is hydrogen, a metal atom or unsubstituted or substituted ammonium, $R^2$ is a saturated or unsaturated straight-chain aliphatic radical of not more than 10 carbon atoms, a cycloaliphatic radical of 3 to 7 carbon atoms, a saturated or unsaturated branched aliphatic radical of 3 to 10 carbon atoms, a halogen-, alkoxy- or alkylmercapto-substituted aliphatic radical of not more than 10 carbon atoms, unsubstituted or halogen-substituted benzyl, or phenyl which is unsubstituted or substituted by halogen or by alkyl of 1 to 4 carbon atoms, and $R^3$ is hydrogen, a saturated or unsaturated straight-chain aliphatic radical of not more than 10 carbon atoms, a cycloaliphatic radical of 3 to 7 carbon atoms, a saturated or unsaturated branched aliphatic radical of 3 to 10 carbon atoms or a halogen- or alkoxy-substituted alkyl radical of 2 to 10 carbon atoms, possess a selective herbicidal action.

Compounds of the formula

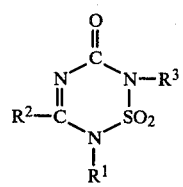
(I)

where $R^1$ is hydrogen, a metal atom or unsubstituted or substituted ammonium, $R^2$ is a saturated or unsaturated straight-chain aliphatic radical of 1 to 10 carbon atoms, a cycloaliphatic radical of 3 to 7 carbon atoms, a saturated or unsaturated branched aliphatic radical of not more than 10 carbon atoms, a halogen-, alkoxy- or alkylmercapto-substituted aliphatic radical of 2 to 10 carbon atoms, unsubstituted or halogen-substituted benzyl, or phenyl which is unsubstituted or substituted by halogen or by alkyl of 1 to 4 carbon atoms, and $R^3$ is hydrogen, a straight-chain aliphatic radical of not more than 10 carbon atoms, a cycloaliphatic radical of 3 to 7 carbon atoms, a branched aliphatic radical of 3 to 10 carbon atoms or a halogen- or alkoxy-substituted alkyl radical of 2 to 10 carbon atoms, with the proviso that $R^2$ is not methyl when $R^1$ is hydrogen and $R^3$ is methyl or isopropyl, and $R^2$ is not phenyl when $R^1$ is hydrogen and $R^3$ is isopropyl, are new.

In formula I, $R^1$ may be, for example, an alkali metal atom, such as sodium or potassium, or ammonium which is unsubstituted or substituted by alkyl or hydroxyalkyl, each of 1 to 10 carbon atoms, or by cycloalkyl of 3 to 7 carbon atoms, such as ammonium, dimethylammonium, triethanolammonium, tridecylammonium, trimethylammonium, diisopropylmethylammonium, diisopropylethylammonium, N-methyl-N,N-diethanolammonium, diisopropylammonium, cyclohexylammonium, polyoxyethylated dimethylammonium, triethylammonium or N,N-dimethyl-N-cyclohexylammonium.

In formula I, $R^2$ may be a saturated or unsaturated straight-chain aliphatic radical of 1 to 10 carbon atoms, a saturated or unsaturated branched aliphatic radical of not more than 10 carbon atoms or a halogen-, alkoxy- or alkylmercapto-substituted aliphatic radical of 2 to 10 carbon atoms, for example a straight-chain alkyl radical of 1 to 10, preferably 2 to 4, carbon atoms, or a branched alkyl radical of 3 to 10 carbon atoms, preferably a branched propyl or butyl radical, e.g. ethyl, n-propyl, isopropyl, n-butyl, isobutyl, sec.-butyl, tert.-butyl, n-pentyl, n-hexyl, pent-3-yl, 1,2-dimethyl-n-propyl, 1,3-dimethyl-n-butyl, 1ethyl-2-methyl-n-propyl, 1,2,2-trimethyl-n-propyl, 1,2-dimethyl-n-hexyl or tert.-amyl, or alkenyl or alkynyl of 3 to 10, preferably 3 or 4, carbon atoms, such as vinyl, alkyl, methallyl, crotyl, 2-ethylhexen-2-yl, hexen-5-yl, 2-methylbuten-2-yl, 2-methylbut-1-en-3-yl, but-1-yn-3-yl, butyn-2-yl, but-1-en-3-yl, propargyl, 2-methylbut-1-en-4-yl, 2-methylbut-2-en-4-yl or 3-methylbut-1-en-3-yl, or haloalkyl, alkoxyalkyl or alkylmercaptoalkyl of 2 to 10, preferably 2 to 4, carbon atoms, such as 2-chloroethyl, 2-chloro-n-propyl, 3chloro-n-propyl, 2-chloroisopropyl, 1-chloromethyl-n-propyl, 2-chlorobut-3-yl, 2-chloro-2-methyl-n-propyl, 2-fluorobut-3-yl, 2-fluoro-2-methyl-n-propyl, 2-fluoroisopropyl, chloro-tert.-butyl, 2,2,2-trifluoroethyl, methoxyethyl, ethoxyethyl, 3-methoxy-n-propyl, methoxyisopropyl, 3-methoxy-n-butyl, 1-methoxybut-2-yl, ethoxy-tert.-butyl, methoxy-tert.-butyl, 2-methoxybutyl, 4-methoxy-n-butyl, methylmercaptoethyl, ethylmercaptoethyl, 3-methylmercapto-n-propyl, 3-methylmercapto-n-butyl, 1-methylmercaptobut-2-yl, methylmercapto-tert.-butyl or 2-methylmercapto-n-butyl, or cycloalkyl of 3 to 7 carbon atoms, such as cyclopropyl, cyclopentyl, cyclohexyl or cycloheptyl, or benzyl which is unsubstituted or substituted in the phenyl ring by halogen, such as fluorine, chlorine, bromine or iodine, e.g. benzyl, 2,6-dichlorobenzyl, 2-chloro-6-fluorobenzyl or 2,6-difluorobenzyl, or phenyl which is unsubstituted or substituted by halogen, such as fluorine, chlorine, bromine or iodine, or by alkyl of 1 to 4 carbon atoms, e.g. phenyl, 4-chlorophenyl, 2,4-dichlorophenyl, 4-isopropylphenyl or 4-tert.-butylphenyl, with the proviso that $R^2$ is not methyl when $R^1$ is hydrogen and $R^3$ is methyl or isopropyl, and that $R^2$ is not phenyl when $R^1$ is hydrogen and $R^3$ is isopropyl.

In formula I, $R^3$ may be hydrogen, a saturated or unsaturated straight-chain aliphatic radical of not more than 10 carbon atoms or a saturated or unsaturated branched aliphatic radical of 3 to 10 carbon atoms, for example a straight-chain alkyl radical of not more than 10, preferably 1 to 4, carbon atoms or a branched alkyl radical of 3 to 10, preferably 3 or 4, carbon atoms, such as methyl, ethyl, n-propyl, isopropyl, n-butyl, isobutyl, sec.-butyl, tert.-butyl, n-pentyl, n-hexyl, pent-3-yl, 1,2-dimethyl-n-propyl, 1,3-dimethyl-n-butyl, 1-ethyl-2-methyl-n-propyl, 1,2,2-trimethyl-n-propyl, 1,2-dimethyl-n-hexyl or tert.-amyl, or alkenyl or alkynyl of 3 to 10 carbon atoms, such as vinyl, allyl, methallyl, crotyl, 2ethylhexen-2-yl, hexen-5-yl, 2-methylbuten-2-yl, 2-methylbut-1-en-3-yl, but-1-yn-3-yl, butyn-2-yl, but-1-en-3-yl, propargyl, 2-methylbut-1-en-4-yl, 2-methylbut-2-en-4-yl or 3-methylbut-1-en-3-yl, or alkyl which is substituted by halogen, such as fluorine, chlorine, bromine or iodine, or may be alkoxyalkyl of 2 to 10, preferably 2 to 4, carbon atoms, e.g. 2-chloroethyl, 2-chloro-n-propyl, 3-chloro-n-propyl, 2-chloroisopropyl, 1-chloromethyl-n-propyl, 2-chlorobut-3-yl, 2-chloro-2-methyl-n-propyl, 2-fluorobut-3-yl, 2-fluoro-2-methyl-n-propyl, 2-fluoroisopropyl, chloro-tert.-butyl, 2,2,2-trifluoroethyl, methoxyethyl, ethoxyethyl, 3-methoxy-n-propyl, methoxyisopropyl, 3-methoxy-n-butyl, 1-methoxybut-2-yl, ethoxy-tert.-butyl, methoxy-tert.-butyl, 2-methoxybutyl or 4-methoxy-n-butyl, or cyclolkyl of 3 to 7 carbon atoms, e.g. cyclopropyl, cyclopentyl, cyclohexyl or cycloheptyl.

Preferred compounds of the formula I are those in which $R^1$ is hydrogen, $R^2$ is alkyl of 1 to 4 carbon atoms and $R^3$ is alkyl of 2 to 4 carbon atoms, with the exception of isopropyl.

The 2H-1,2,4,6-thiatriazin-3-one-1,1-dioxides of the formula I are obtained by reacting an N-carboalkoxyamidine of the formula

where $R^2$ has the above meanings and $R^4$ is alkyl of 1 to 4 carbon atoms, with an aminosulfonyl halide of the formula $$R^3\text{-NHSO}_2Y \qquad (IV)$$

where $R^3$ has the above meanings and Y is fluorine or chlorine, in the presence or absence of an acid acceptor and of an inert organic solvent, at from $-20°$ to $+80°$ C., to give a sulfonyldiamide of the formula

where $R^2$, $R^3$ and $R^4$ have the above meanings, and cyclizing this product in the presence of a basic compound at from 0° to 100° C.

Some of the N-carboalkoxyamidines of the formula III are known, or may be prepared by a conventional method.

If N-carbomethoxyacetamidine and isopropylaminosulfonyl chloride are used as starting materials, the course of the reaction may be represented by the following equation:

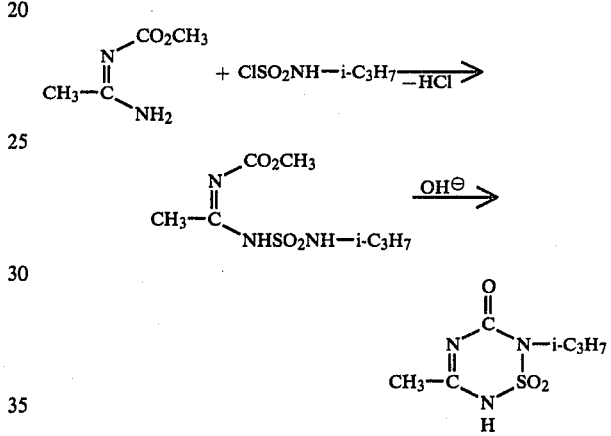

The reaction of the N-carboalkoxyamidine of the formula III with the aminosulfonyl halide of the formula IV may be carried out under atmospheric or superatmospheric pressure, either batchwise or continuously. The sulfonyldiamide of the formula II may be cyclized without being isolated.

Organic solvents which are inert under the reaction conditions are used. Examples of suitable solvents include halohydrocarbons, in particular chlorohydrocarbons, e.g. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, p- and m-dichlorobenzene, o-, p- and m-dibromobenzene, o-, m- and p-chlorotoluene and 1,2,4-trichlorobenzene; ethers, e.g. ethyl propyl ether, methyl tert.-butyl ethyl, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons, e.g. nitromethane, nitroethane, nitrobenzene, o-, m- and p-chloronitrobenzene and o-nitrotoluene; nitriles, e.g. acetonitriles, butyronitriles, isobutyronitrile, benzonitrile and m-chlorobenzonitrile; aliphatic or cycloaliphatic hydrocarbons, e.g. heptane, pinane, nonane, o-, m- and p-cymene, gasoline fractions boiling within a range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, e.g. ethyl acetate, ethyl acetoacetate and isobutyl acetate; amides, e.g. formamide, methylformamide and dimethylformamide; ketones, e.g. acetone and methyl ethyl ketone; and corresponding mixtures. The solvent is advantageously used in an amount of from 100 to 2,000, preferably from 200 to 700, % by weight, based on the starting material III.

The acid acceptors used can be any of the conventional acid-binding agents. These preferably include tertiary amines, alkaline earth metal compounds, ammonium compounds and alkali metal compounds, as well as mixtures of these. However, zinc compounds may also be used. Specific examples of basic compounds which may be used are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, qionoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

Examples of suitable cyclizing agents are the above inorganic acid acceptors, and also alkali metal salts of carboxylic acids, such as sodium propionate, sodium butyrate, sodium isobutyrate, potassium formate, potassium acetate, potassium propionate, potassium butyrate and potassium isobutyrate, and alkali metal alcoholates, such as sodium methylate, sodium ethylate, sodium propylate, sodium isopropylate, sodium butylate, sodium isobutylate, sodium sec.-butylate, sodium tert.-butylate, sodium ethylene-glycolate, sodium-1,2-propylene-glycolate, sodium 1,3-propylene-glycolate, sodium diethylene-glycolate, sodium triethylene-glycolate, sodium 1,2-dipropylene-glycolate, potassium methylate, potassium ethylate, potassium n-propylate, potassium isopropylate, potassium n-butylate, potassium isobutylate, potassium sec.-butylate, potassium tert.-butylate, potassium ethylene-glycolate, potassium 1,2-propylene-glycolate, potassium 1,3-pyropylene-glycolate, potassium diethylene-glycolate, potassium triethylene-glycolate and potassium 1,2-dipropylene-glycolate.

The acid acceptor is advantageously employed in an equivalent amount to the aminosulfonyl halide of the formula IV, or in an excess of not more than 20%.

The cyclization is carried out with the addition of from 1 to 2.5 times the molar amount, based on the sulfonyldiamide of the formula II, of a basic cyclizing agent.

The starting materials of the formulae III and IV are employed in about the stoichiometric ratio, i.e. using from 0.8 to 1.2 moles of the starting material of the formula IV per mole of the starting material of the formula III.

The process is advantageously carried out by running the aminosulfonyl halide of the formula IV and the equivalent amount of acid acceptor, from two separate feeds, into about an equivalent amount of N-carboalkoxyamidine of the formula III in an inert organic solvent at from −20° to +80° C., preferably from 0° to 40° C.

However, it is also possible to take a mixture of the starting material III and the acid acceptor in an inert organic solvent, and then run in the aminosulfonyl halide of the formula IV at from −20° to +80° C., preferably from 0° to 40° C. To complete the reaction, the mixture is stirred for from 0.5 to 8 hours at from −20° to +80° C., preferably from 0° to 40° C.

The reaction mixture is then concentrated, if appropriate, or, in the case of a water-immiscible solvent, is extracted with dilute hydrochloric acid to remove the hydrochlorides, a sulfonyldiamide of the formula II being obtained.

This product may be cyclized in an aqueous medium in the presence of from an equal amount to a 2.5-fold amount of base, or in an organic medium in the presence of from an equal amount to a 2.5-fold amount of alcoholate, to give the desired 2H-1,2,4,6-thiatriazin-3-one-1,1-dioxide salt. To work up the end product, the mixture is then acidified and the precipitate formed is filtered off under suction, if necessary after further concentrating the mixture. The desired end product is thus obtained in a pure form, but can, if desired, be purified by recrystallization or chromatography.

According to their spectroscopic data, the compounds of the formula I, where $R^1$ is hydrogen, occur in the form represented by formula Ia. However, depending on the solvent used, a certain proportion of the tautomeric form Ia' can also be present, both forms being claimed and embraced as equilibrium compounds represented by formula I.

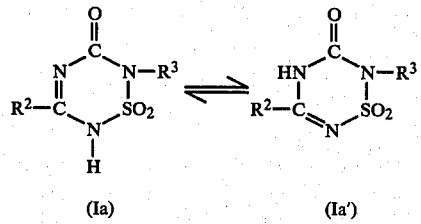

(Ia)    (Ia')

The compounds of the formula Ia not only exhibit herbicidal activity but are also starting materials for the preparation of novel selective herbicides. For example, the substituted 2H-1,2,4,6-thiatriazin-3-one-1,1-dioxides of the formula Ia may be reacted with a halogenating agent to give herbicidal 3-chloro-2H-1,2,4,6-thiatriazin-1,1-dioxides.

EXAMPLE 1

2-Isopropyl-5-methyl-2H-1,2,4,6-thiatriazin-3-one-1,1-dioxide 1010 parts by weight of triethylamine and 157.6 parts by weight of isopropylaminosulfonyl chloride were introduced in the course of 25 minutes, from two separate feeds, into 116 parts by weight of N-carbomethoxyacetamidine in 550 parts by volume of tetrahydrofuran at 20°–25° C., while stirring. Stirring was continued for one hour at 22° C., after which the precipitated hydrochloride was filtered off under suction. The filtrate was washed with tetrahydrofuran and then concentrated, 237 parts by weight (100% of theory) of N-carbomethoxy-N'-isopropylsulfamylacetamidine being obtained as a slightly yellowish oil with $n_D^{25} = 1.4890$.

This oil was dissolved in 700 parts by volume of 3 N sodium hydroxide solution, and the solution was stirred for 3 minutes at 33° C. The aqueous solution was then extracted once with methyl tert.-butyl ether, and stirred into 178 parts by volume of concentrated hydrochloric acid. The product was filtered off under suction, washed with water and dried, and 148 parts by weight (72.2% of theory, based on the starting amidine) of colorless 2-isopropyl-5-methyl-2H-1,2,4,6-thiatriazin-3-one of melting point 193°–196° C. were obtained (active ingredient 1).

EXAMPLE 2

2-Methyl-5-phenyl-2H-1,2,4,6-thiatriazin-3-one-1,1-dioxide 101 parts by weight of methylaminosulfonyl chloride and 61.7 parts by weight of pyridine were introduced, from two separate feeds, into 125 parts by weight of N-carbomethoxybenzamidine in 700 parts by volume of methyl tert.-butyl ether at 10°–20° C., while stirring.

After the mixture had been stirred for 30 minutes at 35° C., the precipitate formed was filtered off under suction and washed with methyl tert.-butyl ether, and the filtrate was concentrated. The residue (190 parts by weight = 100% of theory) of N-carbomethoxy-N'-methylsulfamylbenzamidine was dissolved in 470 parts by volume of 3 N sodium hydroxide solution, and the solution was stirred for 10 minutes at 30°–35° C. The aqueous solution was then extracted once with methyl tert.-butyl ether, and stirred into a mixture of 121 parts by volume of concentrated hydrochloric acid and 500 parts by volume of ice/water. The product was filtered off under suction, washed with water and dried, and 137 parts by weight (82% of theory, based on the starting amidine) of colorless 2-methyl-5-phenyl-2H-1,2,4,6-thiatriazin-3-one-1,1-dioxide, of melting point 246°–249° C. were obtained (active ingredient 2).

EXAMPLE 3

2-Methyl-5-isopropyl-2H-1,2,4,6-thiatriazin-3-one-1,1-dioxide 136 parts by weight of methylaminosulfonyl chloride and 133 parts by weight of N,N-dimethylcyclohexylamine were introduced, from two separate feeds, into a solution of 114 parts by weight of N-carbomethoxyisobutyramidine in 600 parts by volume of methylene chloride at 25°–30° C., and the mixture was stirred for 30 minutes at 20°–25° C. It was then extracted once with water, dried and concentrated, 237 parts by weight (100% of theory) of N-carbomethoxy-N'-methylsulfamylisobutyramidine being obtained as the residue. 125 parts by weight of this residue were dissolved in a solution of 53.7 parts by weight of sodium carbonate in 300 parts by volume of water, and the solution was stirred for 3 minutes at 40° C. and then extracted once with methyl tert.-butyl ether. The solution and 92 parts by volume of concentrated hydrochloric acid were then introduced simultaneously, from two separate feeds, into 100 parts of ice/water, while stirring. The product was filtered off under suction, washed with water and dried, and 77 parts by weight (71% of theory, based on the amount of amidine used) of colorless 2-methyl-5-isopropyl-2H-1,2,4,6-thiatriazin-3-one-1,1-dioxide of melting point 194°–199° C. were obtained (active ingredient 3).

EXAMPLE 4

2-Methyl-5-isopropyl-2H-1,2,4,6-thiatriazin-3-one-1,1-dioxide sodium salt 3.07 parts by weight of 2-methyl-5-isopropyl-2H-1,2,4,6-thiatriazin-3-one-1,1-dioxide were dissolved in a solution of 2.72 parts by weight of a 30% strength sodium methylate in 80 parts of methanol, and the solution was then evaporated to dryness. 3.5 parts by weight (100% of theory) of the sodium salt of 2-methyl-5-isopropyl-2H-1,2,4,6-thiatriazin-3-one-1,1-dioxide of melting point 300° C. were obtained (active ingredient 4).

For example the following compounds were obtained analogously:

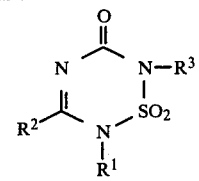

| Compound no. | R¹ | R² | R³ | M.p. [°C.] |
| --- | --- | --- | --- | --- |
| 6 | H | CH₃ | CH₃ | 190–193 |
| 8 | H | CH₃ | C₂H₅ | 208–210 |
| 11 | H | CH₃ | n-C₃H₇ | 164–167 |
| 12 | Na | CH₃ | n-C₃H₇ | 293 (decomposition) |
| 13 | Na | CH₃ | i-C₃H₇ | 298 (decomposition) |
| 19 | H | CH₃ | sec.-C₄H₉ | 154–158 |
| 26 | H | C₂H₅ | CH₃ | 148–150 |
| 38 | H | C₂H₅ | —CH₂—CH₂Cl | 205–208 |
| 40 | H | n-C₃H₇ | CH₃ | 160–163 |
| 50 | H | i-C₃H₇ | n-C₃H₇ | 159–161 |
| 58 | H | i-C₄H₉ | CH₃ | 168–170 |
| 59 | Na | i-C₄H₉ | CH₃ | >320 |
| 70 | Na | phenyl | CH₃ | >320 |
| 79 | Na | CH₃ | CH₃ | 310–320 (decomposition) |
| 80 | Na | CH₃ | sec.-C₄H₉ | 165 (decomposition) |
| 81 | Na | C₂H₅ | ClCH₂—CH₂ | 163 |
| 82 | Na | i-C₃H₇ | n-C₃H₇ | 117 (decomposition) |

For example the following compounds may be obtained analogously:

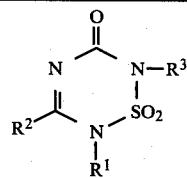

| Compound no. | R¹ | R² | R³ | M.p. [°C.] |
|---|---|---|---|---|
| 5 | H | $CH_3$ | H | |
| 7 | $NH_4$ | $CH_3$ | $CH_3$ | |
| 9 | Na | $CH_3$ | $C_2H_5$ | |
| 10 | $NH_2(CH_2CH_2OH)_2$ | $CH_3$ | $C_2H_5$ | |
| 14 | H | $CH_3$ | n-$C_3H_7$ | |
| 15 | H | $CH_3$ | n-$C_4H_9$ | |
| 16 | Na | $CH_3$ | n-$C_4H_9$ | |
| 17 | H | $CH_3$ | i-$C_4H_9$ | |
| 18 | Na | $CH_3$ | i-$C_4H_9$ | |
| 20 | H | $CH_3$ | tert.-$C_4H_9$ | |
| 21 | Na | $CH_3$ | $C_6H_{11}$ | |
| 22 | H | $CH_3$ | $CH_2CH_2Cl$ | |
| 23 | H | $CH_3$ | —CH—CH—Cl<br>$\phantom{--}$\|$\phantom{---}$\|<br>$\phantom{--}CH_3\phantom{-}CH_3$ | |
| 24 | H | $CH_3$ | $CH_2CH_2$—O—$CH_3$ | |
| 25 | H | $C_2H_5$ | H | |
| 27 | Na | $C_2H_5$ | $CH_3$ | |
| 28 | $NH_2(C_2H_5)_2$ | $C_2H_5$ | $CH_3$ | |
| 29 | H | $C_2H_5$ | $C_2H_5$ | |
| 30 | Na | $C_2H_5$ | $C_2H_5$ | |
| 31 | H | $C_2H_5$ | n-$C_3H_7$ | |
| 32 | H | $C_2H_5$ | i-$C_3H_7$ | |
| 33 | Na | $C_2H_5$ | i-$C_3H_7$ | |
| 34 | H | $C_2H_5$ | n-$C_4H_9$ | |
| 35 | H | $C_2H_5$ | i-$C_4H_9$ | |
| 36 | H | $C_2H_5$ | sec-$C_4H_9$ | |
| 37 | H | $C_2H_5$ | tert.-$C_4H_9$ | |
| 39 | H | n-$C_3H_7$ | H | |
| 41 | H | n-$C_3H_7$ | $C_2H_5$ | |
| 42 | H | n-$C_3H_7$ | i-$C_3H_7$ | |
| 43 | H | n-$C_3H_7$ | n-$C_3H_7$ | |
| 44 | H | n-$C_3H_7$ | n-$C_4H_9$ | |
| 45 | H | n-$C_3H_7$ | sec.-$C_4H_9$ | |
| 46 | Na | n-$C_3H_7$ | $CH_3$ | |
| 47 | H | i-$C_3H_7$ | H | |
| 48 | Na | i-$C_3H_7$ | $CH_3$ | |
| 49 | H | i-$C_3H_7$ | $C_2H_5$ | |
| 51 | H | i-$C_3H_7$ | i-$C_3H_7$ | |
| 52 | H | i-$C_3H_7$ | sec.-$C_4H_9$ | |
| 53 | H | n-$C_4H_9$ | H | |
| 54 | H | n-$C_4H_9$ | $CH_3$ | |
| 55 | Na | n-$C_4H_9$ | $CH_3$ | |
| 56 | H | n-$C_4H_9$ | $C_2H_5$ | |
| 57 | H | i-$C_4H_9$ | H | |
| 60 | H | i-$C_4H_9$ | $C_2H_5$ | |
| 61 | H | i-$C_4H_9$ | n-$C_3H_7$ | |
| 62 | H | i-$C_4H_9$ | i-$C_3H_7$ | |
| 63 | H | sec.-$C_4H_9$ | H | |
| 64 | H | sec.-$C_4H_9$ | $CH_3$ | |
| 65 | Na | sec.-$C_4H_9$ | $CH_3$ | |
| 66 | H | benzyl | H | |
| 67 | H | benzyl | $CH_3$ | |
| 68 | Na | benzyl | $CH_3$ | |
| 69 | H | 4-chlorobenzyl | $CH_3$ | |
| 71 | H | 4-chlorophenyl | $CH_3$ | |
| 72 | H | 2,4-dichloro-phenyl | $CH_3$ | |
| 73 | H | 4-isopropylphenyl | $CH_3$ | |
| 74 | H | $CH_2$=CH | $CH_3$ | |
| 75 | H | $CH_2$=CH—$CH_2$ | $CH_3$ | |
| 76 | H | $CH_3$—CH=CH—$CH_2$ | $CH_3$ | |
| 77 | H | $CH_2$=C—$CH_2$<br>$\phantom{------}$\|<br>$\phantom{------}CH_3$ | $CH_3$ | |

-continued

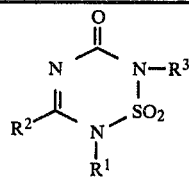

| Compound no. | R¹ | R² | R³ | M.p. [°C.] |
|---|---|---|---|---|
| 78 | H | H—C≡C—CH₂ | CH₃ | |

The compounds of the formula I or Ia may be converted into the usual formulations, e.g. solutions, emulsions, suspensions, dusts, powders, pastes and granules. The forms of application depend entirely on the purpose for which the agents are to be used, but must at all events ensure a fine and uniform distribution of the active ingredient. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene), chlorinated aromatics (e.g., chorobenzenes), paraffins (e.g., petroleum fractions), alcohols (e.g., methanol, butanol), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt % of active ingredient.

The application rates depend on the composition and the growth stages of the weed flora, and are from 0.1 to 15 kg/ha and more, preferably from 0.2 to 5 kg/ha; the higher rates are to be used for total elimination of vegetation.

The novel active ingredients may be applied pre- or postemergence. Preferably, they are applied before or during emergence of the unwanted plants both to cropland and uncropped land.

The agents the ready-to-use formulations made therefrom, e.g., solutions, emulsions, suspensions, powders, dusts, pastes or granules, are applied in known manner, for example by spraying, atomizing, dusting, scattering, seed-disinfecting, or watering.

Examples of formulations are given below.

I. 90 parts by weight of compound 1 is mixed with 10 parts by weight of N-methyl-alpha-pyrrolidone. A mixture is obtained which is suitable for application in the form of very fine drops.

II. 20 parts by weight of compound 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound 26 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound 8 is intimately mixed with 97 parts by weight of particulate kaolin. a dust is obtained containing 3% by weight of the active ingredient.

VII. 30 parts by weight of compound 13 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 38 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt % of active ingredient.

IX. 20 parts of compound 26 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The action of the 2H-1,2,4,6-thiatriazin-3-one-1,1-dioxides of the formula I or Ia on the growth of unwanted and crop plants is demonstrated in greenhouse experiments.

The vessels employed were plastic flowerpots having a volume of 300 cm$^3$, and which were filled with a sandy loam containing about 1.5% humus. In the case of Galium aparine and rice, peat was added to ensure better growth. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate varied, and was either equivalent to 1.0, 2.0 or 4.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. The application rate for postemergence treatment was equivalent to 2.0 kg/ha of active ingredient per hectare.

The pots were set up in the greenhouse—species from warmer areas at from 20° to 30° C., and species from moderate climates at 15° to 25° C. The experiments were run for from 3 to 5 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Amaranthus spp., Chenopodium album, Datura stramonium, Galium aparine, Matricaria spp., Nicandra physaloides, Oryza sativa, Sinapis alba, Solanum nigrum, Zea mays, Gossypium hirsutum,* and *Triticum aestivum.*

In investigations into the herbicidal action on preemergence application, for example compound No. 6, applied at a rate of 1.0 kg/ha, had a good action on unwanted plants. In investigtions into the herbicidal action on preemergence application, compound No. 26 had a good action on unwanted plants. For example compound No. 8, at 4.0 kg/ha, also had a good action on broadleaved unwanted plants. Important crop plant species remained unaffected.

In tests with the herbicidal agents on postemergence application, for example compound No. 26, at 2.0 kg/ha, selectively combatted broadleaved weeds in crop plants such as rice and cotton.

In view of the many application methods possible, the agents, or mixtures containing them, can be used in a further, large number of crops for removing unwanted plant growth.

The following crops may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asaparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* | parsley |
| spp. *tuberosum* | |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. *vulgare*) | sorghum |
| *Sorghum dochna* | |
| *Spinacia oleracea* | spinach |
| *Theobroma cacao* | cacao plants |

-continued

| Botanical name | Common name |
| --- | --- |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines 4H-3,1-benzoxazine derivatives, benzothiadiazinones, 2,6-dinitroanilines, N-phenylcarbamates, thiolcarbamates, halocarboxylic acids, triazines, amides ureas, diphenyl ethers, triazinones, uracils, benzofuran derivatives, cyclohexane-1,3-dione derivatives, etc.

It may also be useful to apply the compounds according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies.

To initiate the herbicidal action, wetting agents, spreader-stickers and non-phytotoxic oils and oil concentrates may also be added.

We claim:

1. A 2H-1,2,4,6-thiatriazin-3-one-1,1-dioxide of the formula

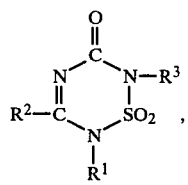

(I)

where $R^1$ is hydrogen, a metal atom or unsubstituted or substituted ammonium, $R^2$ is a saturated or unsaturated straight-chain aliphatic radical of not more than 10 carbon atoms, a cycloaliphatic radical of 3 to 7 carbon atoms, a saturated or unsaturated branched aliphatic radical of not more than 10 carbon atoms, a halogen-, alkoxy- or alkylmercapto-substituted aliphatic radical of 2 to 10 carbon atoms, unsubstituted or halogen-substituted benzyl, or phenyl which is unsubstituted or substituted by halogen or by alkyl of 1 to 4 carbon atoms, and $R^3$ is hydrogen, a saturated or unsaturated straight-chain aliphatic radial of not more than 10 carbon atoms, a cycloaliphatic radical of 3 to 7 carbon atoms, a saturated or unsaturated branched aliphatic radical of 3 to 10 carbon atoms or a halogen- or alkoxy-substituted alkyl radical of 2 to 10 carbon atoms, with the proviso that $R^2$ is not methyl when $R^1$ is hydrogen and $R^3$ is methyl or isopropyl, and $R^2$ is not phenyl when $R^1$ is hydrogen and $R^3$ is isopropyl.

2. A 2H-1,2,4,6-thiatriazin-3-one-1,1-dioxide of the formula I as claimed in claim 1, where $R^1$ is hydrogen, $R^2$ is alkyl of 1 to 4 carbon atoms, and $R^3$ is alkyl of 2 to 4 carbon atoms with the exception of isopropyl.

3. 2-Methyl-5-ethyl-2H-1,2,4,6-thiatriazin-3-one-1,1-dioxide.

4. 2-Ethyl-5-methyl-2H-1,2,4,6-thiatriazin-3-one-1,1-dioxide.

5. A herbicide containing inert additives and a 2H-1,2,4,6-thiatriazin-3-one-1,1-dioxide of the formula

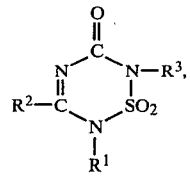

(Ia)

where $R^1$ is hydrogen, a metal atom or unsubstituted or substituted ammonium, $R^2$ is a saturated or unsaturated straight-chain aliphatic radical of not more than 10 carbon atoms, a cycloaliphatic radical of 3 to 7 carbon atoms, a saturated or unsaturated branched aliphatic radical of 3 to 10 carbon atoms, a halogen-, alkoxy- or alkylmercapto-substituted aliphatic radical of not more than 10 carbon atoms, unsubstituted or halogen-substituted benzyl, or phenyl which is unsubstituted or substituted by halogen or by alkyl of 1 to 4 carbon atoms, and $R^3$ is hydrogen, a saturated or unsaturated straight-chain aliphatic radical of not more than 10 carbon atoms, a cycloaliphatic radical of 3 to 7 carbon atoms, a saturated or unsaturated branched aliphatic radical of 3 to 10 carbon atoms or a halogen- or alkoxy-substituted alkyl radical of 2 to 10 carbon atoms.

6. A herbicide containing inert additives and a 2H-1,2,4,6-thiatriazin-3-one-1,1-dioxide of the formula

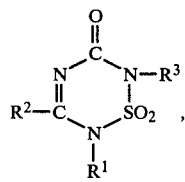

(I)

where $R^1$ is hydrogen, a metal atom or unsubstituted or substituted ammonium, $R^2$ is a saturated or unsaturated straight-chain aliphatic radical of not more than 10 carbon atoms, a cycloaliphatic radical of 3 to 7 carbon atoms, a saturated or unsaturated branched aliphatic radical of not more than 10 carbon atoms, a halogen-, alkoxy- or alkylmercapto-substituted aliphatic radical of 2 to 10 carbon atoms, unsubstituted or halogen-substituted benzyl, or phenyl which is unsubstituted or substituted by halogen or by alkyl of 1 to 4 carbon atoms, and $R^3$ is hydrogen, a saturated or unsaturated straight-chain aliphatic radical of not more than 10 carbon atoms, a cycloaliphatic radical of 3 to 7 carbon atoms, a saturated or unsaturated branched aliphatic radical of 3 to 10 carbon atoms or a halogen- or alkoxy-substituted alkyl radical of 2 to 10 carbon atoms, with the proviso that $R^2$ is not methyl when $R^1$ is hydrogen and $R^3$ is methyl or isopropyl, and $R^2$ is not phenyl when $R^1$ is hydrogen and $R^3$ is isopropyl.

7. A herbicide containing inert additives and a 2H-1,2,4,6-thiatriazin-3-one-1,1-dioxide of the formula I as claimed in claim 1, $R^1$ denoting hydrogen, $R^2$ alkyl of 1 to 4 carbon atoms and $R^3$ alkyl of 2 to 4 carbon atoms with the exception of isopropyl.

8. A herbicide containing inert additives and, as active ingredient, 2,5-dimethyl-2H-1,2,4,6-thiatriazin-3-one-1,1-dioxide.

9. A process for combating the growth of unwanted plants, wherein the plants or the soil are treated with a herbicidally effective amount of a 2H-1,2,4,6-thiatriazin-3-one-1,1-dioxide of the formula Ia as claimed in claim 5.

* * * * *